US010781146B2

(12) United States Patent
Watanabe et al.

(10) Patent No.: US 10,781,146 B2
(45) Date of Patent: Sep. 22, 2020

(54) PROCESS FOR PREPARING A 5-ALKEN-1-YNE COMPOUND, (6Z)-1,1-DIALKOXY-6-NONEN-2-YNE COMPOUND, (2E,6Z)-2,6-NONADIENAL AND (2E)-CIS-6,7-EPOXY-2-NONENAL, AND 1,1-DIALKOXY-6-NONEN-2-YNE COMPOUND

(71) Applicant: SHIN-ETSU CHEMICAL CO., LTD., Tokyo (JP)

(72) Inventors: Tomohiro Watanabe, Niigata (JP); Takeshi Kinsho, Niigata (JP); Yuki Miyake, Niigata (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 0 days.

(21) Appl. No.: 16/533,254

(22) Filed: Aug. 6, 2019

(65) Prior Publication Data
US 2020/0048161 A1 Feb. 13, 2020

(30) Foreign Application Priority Data

Aug. 10, 2018 (JP) .................................. 2018-151661

(51) Int. Cl.
*C07D 301/03* (2006.01)
*C07C 1/32* (2006.01)
*C07C 41/01* (2006.01)
*C07C 41/20* (2006.01)
*C07C 43/15* (2006.01)
*C07C 45/42* (2006.01)
*C07F 1/00* (2006.01)
*C07F 1/02* (2006.01)
*C07F 1/04* (2006.01)
*C07F 3/02* (2006.01)
*C07F 7/08* (2006.01)

(52) U.S. Cl.
CPC .............. *C07C 1/321* (2013.01); *C07C 41/01* (2013.01); *C07C 41/20* (2013.01); *C07C 43/15* (2013.01); *C07C 45/42* (2013.01); *C07D 301/03* (2013.01); *C07F 1/00* (2013.01); *C07F 1/02* (2013.01); *C07F 1/04* (2013.01); *C07F 3/02* (2013.01); *C07F 7/083* (2013.01)

(58) Field of Classification Search
CPC ......... C07C 1/321; C07C 41/01; C07C 45/42; C07C 43/15; C07C 41/20; C07F 3/02; C07F 1/00; C07F 1/04; C07F 1/02; C07F 7/083; C07D 301/03
USPC ....................................................... 549/523
See application file for complete search history.

(56) References Cited

PUBLICATIONS

Crombie et al , Amides of vegetable Origin. Part VII. synthesis of N-isobutyldodecatrans-2: trans-4;trans-8- and trans-2:trans-4:cis-8- trienamide and Their Relation to Sanshool I., Journal of the Chemical Society, 1955, p. 4244-4249. (Year: 1955).*
Speck et al. "Sequential O—H/C—H Bond Insertion of Phenols Initiated by the Gold(I)-Catalyzed Cyclization of 1-Bromo-1,5-enynes" Organic Letters, 17(8):1982-1985 (2015).
Crombie et al. "Amides of Vegetable Origin. Part VII. Synthesis of N-isoButyldodeca-trans-2: trans-4: trans-8- and trans-2: trans-4: cis-8-trienamide and Their Relation to Sanshool I" Journal of the Chemical Society, pp. 4244-4249 (1955).
Extended European Search Report corresponding to European Patent Application No. 19191122.1 (9 pages) (dated Dec. 19, 2019).
Mori et al. "Stereoselective Synthesis of the Pink Bollworm Sex Pheromone, (Z, Z)-7,11-Hexadecadienyl Acetate and its (Z, E)-Isomer" Tetrahedron, 31:1846-1848 (1975).
Mukai et al. "Base-Catalyzed Endo-Mode Cyclization of Allenes: Easy Preparation of Five- to Nine-Membered Oxacycles" Journal of Organic Chemistry, 69(20):6867-6873 (2004).
Murakami et al. "Efficient stereocontrolled synthesis of sphingadienine derivatives" Tetrahedron, 61:9233-9241 (2005).
Mori et al. "Synthesis of (4E,8E,2S,3R,2'R)-N-2'-Hydroxyhexadecanoyl-1-0-beta-Glucopyranosyl-9-Methyl-4,8-Sphingadienine, The Fruiting-Induced Cerebroside in a Basidiomycete Schizophyllum Commune" Tetrahedron, 41(12):2379-2386 (1985).
Mori, Kenji "Pheromone synthesis. Part 263: Synthesis of the racemate and the enantiomers of (E)-cis-6,7-epoxy-2-nonenal, the male-produced pheromone of the red-necked longhorn beetle, Aromia bungii" Tetrahedron, 74:1444-1448 (2018).
Speck et al. "Sequential O—H/C—H Bond Insertion of Phenols Initiated by the Gold(I)-Catalyzed Cyclization of 1-Bromo-1,5-Enynes" Organic Letters, 17(8):1982-1985 (2015) (Abstract & supplemental information only).
Xu et al. "Identification of a male-produced sex-aggregation pheromone for a highly invasive cerambycid beetle, Aromia bungii"Scientific Reports, 7(7330):1-7 (2017).

* cited by examiner

*Primary Examiner* — Taylor V Oh
(74) *Attorney, Agent, or Firm* — Myers Bigel, P.A.

(57) ABSTRACT

The object of the present invention is to provide a process for preparing a 5-alken-1-yne compound efficiently at low costs and a process for preparing (2E,6Z)-2,6-nonadienal by making use of the aforesaid process for preparing the 5-alken-1-yne compound.

There is provided a process for preparing a 5-alken-1-yne compound of the following formula (4): Y—Z—CR$^1$=CR$^2$—(CH$_2$)$_2$—C≡CH (4) in which Y in formula (4) represents a hydrogen atom or a hydroxyl group, the process comprising at least steps of: subjecting (i) an alkenylmagnesium halide compound prepared from a haloalkene compound of the following formula (1): Y—Z—CR$^1$=CR$^2$—(CH$_2$)$_2$—X$^1$ (1) and (ii) an alkyne compound of the following formula (2): X$^2$—C≡C—Si(R$^3$)(R$^4$)(R$^5$) (2) to a coupling reaction to form a silane compound of the following formula (3): Y—Z—CR$^1$=CR$^2$—(CH$_2$)$_2$—C≡C—Si(R$^3$)(R$^4$)(R$^5$) (3); and subjecting the silane compound (3) to a desilylation reaction to form the 5-alken-1-yne compound (4).

5 Claims, No Drawings

PROCESS FOR PREPARING A 5-ALKEN-1-YNE COMPOUND, (6Z)-1,1-DIALKOXY-6-NONEN-2-YNE COMPOUND, (2E,6Z)-2,6-NONADIENAL AND (2E)-CIS-6,7-EPOXY-2-NONENAL, AND 1,1-DIALKOXY-6-NONEN-2-YNE COMPOUND

TECHNICAL FIELD

The present invention relates to a process for preparing a 5-alken-1-yne compound, a process for preparing a (6Z)-1,1-dialkoxy-6-nonen-2-yne compound, (2E,6Z)-2,6-nonadienal, and (2E)-cis-6,7-epoxy-2-nonenal, by making use of the aforesaid process for preparing the 5-alken-1-yne compound, and a 1,1-dialkoxy-6-nonen-2-yne compound.

BACKGROUND ART

Organic compounds having an enyne skeleton which has a triple bond and a double bend which are bonded together via a methylene group(s) are often seen as natural products such as bioactive substances and pheromone. Accordingly, intermediates having the enyne skeleton are very useful.

A 5-alken-1-yne compound which is one of the organic compounds having a triple bond and a double bond bonded together via two methylene groups has an ethynyl group at the position of a homoallyl. As a process for preparing a 5-alken-1-yne compound, Mori et al. make (3E)-4-bromo-3-tridecene to react with potassium cyanide to form a nitrile, which is then reduced into an aldehyde and reacted with carbon tetrabromide to form a dibromo-olefin, which is subsequently reacted with n-butyllithium to give the 5-alken-1-yne compound (Non-Patent Document 1). Magauer et al. produce the 5-alken-1-yne compound by reacting 5-bromo-2-methylpentene with a lithium acetylide-ethylenediamine complex (Non-Patent Document 2).

Red-necked longhorn beetle (*Aromia bungli*) native to China, Taiwan, the Korean Peninsula, and northern. Vietnam is a pest which has invaded into Japan in recent years and damages cherry, persimmon, olive, peach, Japanese apricot, pomegranate, and willow trees. A large number of cherry trees have already been damaged in japan. If the red-necked longhorn beetle spreads throughout Japan, a total damage is estimated to be 22 billion yens. The Ministry of Agriculture, Forestry and Fisheries and the Ministry of Land in Japan are trying to control the red-necked longhorn beetle, but an effective control method has not yet been established. Control or survey of emergence of this beetle with its aggregation pheromone has attracted attention and is expected to be successful.

An aggregation pheromone of the red-necked longhorn beetle is found to be (2E)-cis-6,7-epoxy-2-nonenal (Non-Patent Document 3). It has been reported that (2E)-cis-6,7-epoxy-2-nonenal can be synthesized by epoxidizing (2Z)-2-penten-1-ol to form 2,3-epoxy-1-pentanol, converting the 2,3-epoxy-1-pentanol thus obtained into a triflate, and then subjecting the triflate to a coupling reaction with an allyl Grignard reagent, followed by olefin metathesis with 2-butenal (Non-Patent Document 4).

LIST OF THE PRIOR ART

[Non-Patent Document 1] K. Mori et al., Tetrahedron. 1985, 41, p. 2379.
[Non-Patent Document 2] T. Magauer et al., Org. Lett 2015, 17, p. 1982,
[Non-Patent Document 3] H. Yasui et al., Scientific Reports, 2017, 7(1), p. 7330.
[Non-Patent Document 4] K. Mori, Tetrahedron. 2018, 74, p. 1444.

SUMMARY OF THE INVENTION

However, according to the process in Non-Patent Document 1, the conversion of the homoallyl halide into the 5-alken-1-yne compound requires four steps, and the nitrile is p prepared using highly toxic sodium cyanide. In addition, the reduction of the nitrite into an aldehyde and the reaction between dibromo-olefin and n-butyllithium are carried out at −60° C. and −78° C., respectively, and these cannot be carried out in usual reaction equipments. The method described in Non-Patent Document 2 is not suited for industrial production, because the ethynylation is carried out using an expensive lithium acetylide-ethylenediamine complex. The method described in Non-Patent Document 4 suffers from poor productivity and has difficulty in mass production in an industrial scale, because an expensive Grubbs catalyst is used and the olefin metathesis is carried out with a large amount of a solvent and 2-butenal to prevent out homometathesis. Further, a total yield over the four steps starting from (2Z)-2-penten-1-ol is so low as 6.6%.

The present invention has been made in these circumstances, and aims to overcome the aforesaid problems of the prior art, and to provide a process for preparing a 5-alken-1-yne compound efficiently at low costs, a process for preparing a (6Z)-1,1-dialkoxy-6-nonen-2-yne compound, (2E,6Z)-2,6-nonadienal, and (2E)-cis-6,7-epoxy-2-nonenal, by making use of the aforesaid process for preparing the 5-alken-1-yne compound, and to provide a 1,1-dialkoxy-6-nonen-2-yne compound.

As a result of the intensive researches, the present inventors have found that a 5-alken-1-yne compound can be prepared efficiently at low costs by carrying out a coupling reaction of (i) an alkenylmagnesium halide compound prepared from a haloalkene compound with (ii) an alkyne compound, and a subsequent desilylation reaction. Further, the present inventors have found that a (6Z)-1,1-dialkoxy-6-nonen-2-yne compound, (2E,6Z)-2,6-nonadienal, and (2E)-cis-6,7-epoxy-2-nonenal can be efficiently prepared by making use of the aforesaid process for preparing the 5-alken-1-yne compound. Thus, the present invention has been completed.

In one aspect of the present invention, there is provided a process for preparing a 5-alken-1-yne compound of the following formula (4):

$$Y\text{---}Z\text{---}CR^1\!\!=\!\!CR^2\text{---}(CH_2)_2\text{---}C\!\!\equiv\!\!CH \qquad (4)$$

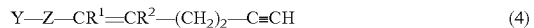

in which Y in formula (4) represents a hydrogen atom or a hydroxyl group, Z represents a divalent hydrocarbon group having from 1 to 15 carbon atoms, and $R^1$ and $R^2$ represent, each independently, a hydrogen atom or a monovalent hydrocarbon group having from 1 to 6 carbon atoms or bond together to form a divalent hydrocarbon group having from 1 to 6 carbon atoms, $R^1$-$R^2$, the process comprising at least steps of:

subjecting (i) an alkenylmagnesium halide compound prepared from a haloalkene compound of the following formula (1):

$$Y\text{---}Z\text{---}CR^1\!\!=\!\!CR^2\text{---}(CH_2)_2\text{---}X^1 \qquad (1)$$

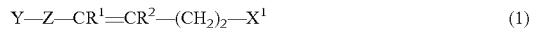

in which Y, Z, $R^1$ and $R^2$ are as defined above and $X^1$ represents a halogen atom; and (ii) an alkyne compound of the following formula (2):

$$X^2\text{---}C\!\!\equiv\!\!C\text{---}Si(R^3)(R^4)(R^5) \qquad (2)$$

in which $X^2$ represents a halogen atom, $R^3$ represents a hydrogen atom or a monovalent hydrocarbon group having from 1 to 6 carbon atoms and $R^4$ and $R^5$ represent, each independently, a monovalent hydrocarbon group having from 1 to 6 carbon atoms or bond together to represent a divalent hydrocarbon group having from 2 to 6 carbon atoms, $R^4$-$R^5$, to a coupling reaction to form a silane compound of the following formula (3):

Y—Z—CR$^1$=CR$^2$—(CH$_2$)$_2$—C≡C—Si(R$^3$)(R$^4$)(R$^5$)   (3)

in which Y, Z, $R^1$, $R^2$, $R^3$, $R^4$, and $R^5$ are as defined above; and subjecting the silane compound (3) to a desilylation reaction to form the 5-alken-1-yne compound (4).

In another aspect of the present invention, there is also provided a process for preparing a (6Z)-1,1-dialkoxy-6-nonen-2-yne compound of the following formula (7a):

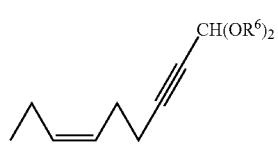

(7a)

in which $R^4$ may be the same or different at each occurrence and represents a monovalent hydrocarbon group having from 1 to 6 carbon atoms, the process comprising at least steps of:

each of the steps of the aforesaid process for preparing a 5-alken-1-yne compound of formula (4) in which Y represents a hydrogen atom, Z represents an ethylene group, and $R^1$ and $R^2$ each represent a hydrogen atom, that is, (5Z)-5-octen-1-yne of the following formula (4-1):

(4-1)

preparing, from the (5Z)-5-octen-1-yne (4-1) thus obtained, an acetylide compound of the following formula (5):

(5)

in which M represents Li, Na, K, or MgX$^3$, and X$^3$ represents a halogen atom; and subjecting the acetylide compound (5) and an orthoformic acid ester compound of the following formula (6):

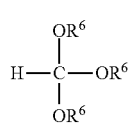

(6)

in which $R^6$ may be the same or different at each occurrence and represents a monovalent hydrocarbon group having from 1 to 6 carbon atoms, to a nucleophilic substitution reaction to form the (6Z)-1,1-dialkoxy-6-nonen-2-yne compound (7a).

In a further aspect of the present invention, there is also provided a process for preparing (2E,6Z)-2,6-nonadienal of the following formula (9):

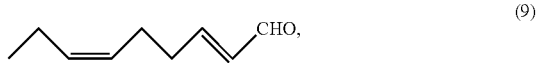

(9)

the process comprising at least steps of:

each of the steps of the aforesaid process for preparing a (6Z)-1,1-dialkoxy-6-nonen-2-yne compound (7a);

subjecting the (6Z)-1,1-dialkoxy-6-nonen-2-yne compound (7a) thus obtained to a reduction reaction to form a (6Z)-1,1-dialkoxy-2,6-nonadiene compound of the following formula (8):

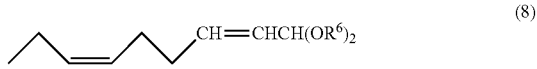

(8)

in which $R^6$ may be the same or different at each occurrence and represents a monovalent hydrocarbon group having from 1 to 6 carbon atoms; and hydrolyzing, the (6Z)-1,1-dialkoxy-2,6-nonadiene compound (8) to form (2E,6Z)-2,6-nonadienal (9).

In a still further aspect of the present invention, there is also provided a process for preparing (2E)-cis-6,7-epoxy-2-nonenal of the following formula (10):

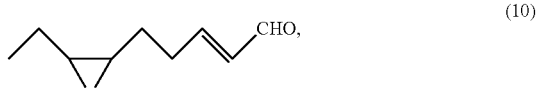

(10)

the process comprising at least steps of:

each of the steps of the aforesaid process for preparing (2E,6Z)-2,6-nonadienal (9); and epoxidizing (2E,6Z)-2,6-nonadienal (9) thus obtained to form (2E)-cis-6,7-epoxy-2-nonenal (10).

In a still further aspect of the present invention, there is also provided a 1,1-dialkoxy-6-nonen-2-yne compound of the following formula (7):

CH$_3$CH$_2$CH=CH—(CH$_2$)$_2$—C≡C—CH(OR$^6$)$_2$   (7)

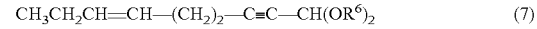

in which $R^6$ may be the same or different at each occurrence and represents a monovalent hydrocarbon group having front 1 to 6 carbon atoms.

The present invention makes it possible to efficiently prepare the 5-alken-1-yne compound at low costs. Further, the (6Z)-1,1-dialkoxy-6-nonen-2-yne compound, (2E,6Z)-2,6-nonadienal, and (2E)-cis-6,7-epoxy-2-nonenal can be prepared efficiently at low costs, by making use of the aforesaid process for preparing the 5-alken-1-yne compound.

The 1,1-dialkoxy-6-nonen-2-yne compound is useful as an intermediate in organic synthesis.

DETAILED DESCRIPTION OF THE INVENTION

First, in the process for preparing a 5-alken-1-yne compound, the step of subjecting (i) an alkenylmagnesium halide compound prepared from a haloalkene compound of the following formula (1); and (ii) an alkyne compound of the following formula (2) to a coupling reaction to form a silane compound of the following formula (3) will be described hereinafter.

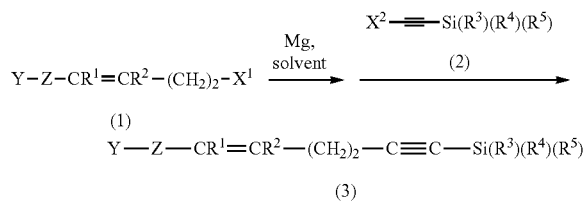

$$Y-Z-CR^1=CR^2-(CH_2)_2-X^1 \xrightarrow[\text{solvent}]{\text{Mg,}} \quad X^2-\!\!\equiv\!\!-Si(R^3)(R^4)(R^5) \quad (2)$$

(1)

$$Y-Z-CR^1=CR^2-(CH_2)_2-C\equiv C-Si(R^3)(R^4)(R^5)$$

(3)

Y in formula (1) represents a hydrogen atom or a hydroxyl group. When Y represents a hydroxyl group, this may be protected with a protecting group if necessary. Examples of the protecting group include protecting ether groups such as methyl, benzyl, p-methoxybenzyl, and 2-naphthylmethyl groups; protecting acetal groups having from 2 to 12 carbon atoms such as methoxymethyl, 2-tetrahydropyranyl, 1-ethoxyethyl, benzyloxymethyl, p-methoxybenzyloxymethyl, and 2-naphthylmethyloxymethyl groups; and protecting silylether groups such as trimethylsilyl, triethylsilyl, t-butyldimethylsilyl, triisopropylsilyl, and t-butyldiphenylsilyl groups.

Z in formula (1) represents a divalent hydrocarbon group having front 1 to 15, preferably from 1 to 12, carbon atoms.

Examples of the divalent hydrocarbon group, Z, include linear saturated hydrocarbon groups such as methylene, ethylene, 1,3-propylene, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 1,13-tridecylene, 1,14-tetradecylene, and 1,15-pentadecylene groups; branched, saturated hydrocarbon groups such as 1,2-propylene, 2,2-dimethyl-1,3-propylene, 1,2-butylene, 1,3-butylene, 2,3-butylene, and 2,3-dimethyl-2,3-butylene groups; linear unsaturated hydrocarbon groups such as 1-vinylethylene group; branched unsaturated hydrocarbon groups such as 2-methylene-1,3-propylene groups; and cyclic hydrocarbon groups such as 1,2-cyclopropylene and 1,2-cyclobutylene groups. Hydrocarbon groups having isomeric relation with the aforesaid ones are also included. A part of hydrogen atoms of the hydrocarbon group may be substituted with a methyl or ethyl group.

$R^1$ and $R^2$ in formula (1) represent, each independently, a hydrogen atom or a monovalent hydrocarbon group having from 1 to 6 carbon atoms, preferably 1 or 2 carbon atoms or bond together to form a divalent hydrocarbon group having from 1 to 6 carbon atoms, more preferably from 3 to 6 carbon atoms, $R^1$-$R^2$.

Examples of the monovalent hydrocarbon group, $R^1$ or $R^2$, include linear saturated hydrocarbon groups such as methyl, ethyl, n-propyl, n-butyl, n-pentyl, and n-hexyl groups; branched saturated hydrocarbon groups such as isopropyl, 2-methylbutyl, and t-butyl groups; branched unsaturated hydrocarbon groups such as 2-methyl-2-propenyl group; cyclic saturated hydrocarbon groups such as cyclopropyl group; and aryl groups such as phenyl group. Hydrocarbon groups having isomeric relation with the aforesaid ones are also included. A part of hydrogen atoms of the hydrocarbon group may be substituted with a methyl or ethyl group.

Examples of the divalent hydrocarbon group, $R^1$-$R^2$, include linear saturated hydrocarbon groups such as methylene, ethylene, 1,3-propylene, 1,4-butylene, 1,5-pentylene, and 1,6-hexylene groups; branched saturated hydrocarbon groups such as 1,2-propylene, 2,2-dimethyl-1,3-propylene, 2-butylene, 1,3-butylene, 2,3-butylene, and 2,3-dimethyl-2, 3-butylene groups; linear unsaturated hydrocarbon groups such as 1-vinylethylene group; branched unsaturated hydrocarbon groups such as 2-methylene-1,3-propylene group; and cyclic hydrocarbon groups such as 1,2-cyclopropylene and 1,2-cyclobutylene groups. Hydrocarbon groups having isomeric relation with the aforesaid ones are also included. A part of hydrogen atoms of the hydrocarbon group may be substituted with a methyl or ethyl group.

$X^1$ in formula (1) represents a halogen atom. Examples of the halogen atom for $X^1$ include chlorine, bromine, and iodine atoms. A chlorine or bromine atom is preferred among these in view of the easy preparation of a Grignard reagent.

Examples of a geometric isomer of —$CR^1$=$CR^2$— in the haloalkene compound of formula (1) include (E) an 1 (Z) isomers. Examples of the haloalkene compound (1) include 1-halo-3-hexene compounds such as (3Z)-1-chloro-3-hexene and (3E)-1-chloro-3-hexene; 1-halo-3-octene compounds such as (3E)-1-chloro-3-octene; 1-halo-3-tetradecene compounds such as (3Z)-1-chloro-3-tetradecene; and 1-halo-6-[(tetrahydro-2H-pyran-2-yl)oxy]-3-hexene compounds such as (3 Z)-1-chloro-6-[(tetrahydro-2H-pyran-2-yl)oxy]-3-hexene. The halo-alkene compound (1) may be commercially available or may be synthesized in house.

An alkenylmagnesium halide compound is prepared from the haloalkene compound (1). The alkenylmagnesium halide compound can be prepared by reacting the haloalkene compound (1) with magnesium in a solvent.

An amount of magnesium used in preparing an alkenylmagnesium halide compound from the haloalkene compound (1) is preferably from 1.0 to 2.0 gram atoms (from 24.3 to 48.6 g) per mol of the haloalkene compound (1) in view of the completion of the reaction.

Examples of a solvent used in preparing an alkenylmagnesium halide compound from the haloalkene compound (1) include ether solvents such as tetrahydrofuran, diethyl ether, and 4-methyltetrahydropyran, and hydrocarbon solvents such as toluene, xylene, and hexane. Tetrahydrofuran is preferred among these in view of the reaction rate for the formation of a Grignard reagent. The solvent may be used either alone or in combination thereof. The solvent may be commercially available one. An amount of the solvent is preferably from 50 to 600 g per mol of the haloalkene compound (1) in view of the reactivity.

A reaction temperature in preparing an alkenylmagnesium halide compound from the haloalkene compound (1) differs, depending on a solvent used, and is preferably 30 to 120° C. in view of the reactivity. A reaction time in preparing an alkenylmagnesium halide compound from the haloalkene compound (1) differs, depending on a solvent used or a production scale, and is preferably 1 to 30 hours in view of the reactivity.

Examples of the alkenylmagnesium halide compound include 3-hexenylmagnesium halide compounds such as (3Z)-3-hexenylmagnesium chloride and (3E)-3-hexenylmagnesium chloride, 3-octenylmagnesium halide compounds such as (3Z)-3-octenylmagnesium chloride, 3-tetradecenylmagnesium halide compounds such as (3Z)-3-tetradecenylmagnesium chloride, and 6-[(tetrahydro-2H-pyran-2-yl)oxy]-3-hexenylmagnesium halide compounds such as (3Z)-6-[(tetrahydro-2H-pyran-2-yl)oxy]-3-hexenylmagnesium chloride.

$X^2$ in formula (2) represents a halogen atom and examples of it are the same as those for $X^1$ and it may be the same as or different from $X^1$. As the halogen atom for $X^2$, a bromine or iodine atom is preferred in view of the easy preparation and the easy availability of the alkyne compound.

$R^3$ in formula (2) represents a hydrogen atom or a monovalent hydrocarbon group having from 1 to 6 carbon atoms. Examples of the monovalent hydrocarbon group, $R^3$, are the same as those of the monovalent hydrocarbon group as $R^1$ or $R^2$.

$R^4$ and $R^5$ in formula (2) represent, each independently, a monovalent hydrocarbon group having from 1 to 6 carbon atoms or bond together to represent a divalent hydrocarbon group having from 2 to 6 carbon atoms, preferably from 3 to 6 carbon atoms, $R^4$-$R^5$.

Examples of the monovalent hydrocarbon group, $R^4$ or $R^5$, are the same as those of the monovalent hydrocarbon group as $R^1$ or $R^2$. Examples of the divalent hydrocarbon group, $R^4$-$R^5$, are the same as those for $R^1$-$R^2$.

Examples of the alkyne compound (2) include (2-haloethynyl)silane compounds such as (2-chloroethynyl)silane compounds, (2-bromoethynyl)silane compounds, and (2-iodoethynyl)silane compounds. Although (2-chloroethynyl) silane compounds are excellent in stability and (2-iodoethynyl)silane compounds are excellent in reactivity, (2-bromoethynyl)silane compounds are excellent in both stability and reactivity and more preferred. The alkyne compound (2) may be commercially available one or may be synthesized in house.

Examples of the (2-chloroethynyl)silane compounds include (2-chloroethynl)trimethylsilane, (2-chloroethynyl) triethylsilane, (2-chloroethynyl)-t-butyldimethylsilane, (2-chloroethynyl)triisopropylsilane, and (2-chloroethynyl)-t-butyldiphenylsilane.

Examples of the (2-bromoethynyl)silane compound include (2-bromoethynyl)trimethylsilane, (2-bromoethynyl) triethylsilane, (2-bromoethynyl)-t-butyldimethylsilane, (2-bromoethynyl)triisopropylsilane, and (2-bromoethynyl)-t-butyldiphenylsilane.

Examples of the (2-iodoethynyl)silane compound include (2-iodoethynyl)trimethylsilane, (2-iodoethynyl)triethylsilane (2-iodoethynyl)-t-butyldimethylsilane, (2-iodoethynyl) triisopropylsilane, and (2-iodoethynyl)-t-butyldiphenylsilane In view of the easy preparation and the easy availability, the alkyne compound (2) is preferably a (2-bromoethynyl) trialkylsilane compound such as (2-bromoethynyl)trimethylsilane, (2-bromoethynyl)triethylsilane, (2-bromoethynyl)-t-butyldimethylsilane, or (2-bromoethynyl) triisopropylsilane; or a (2-iodoethynyl)trialkylsilane compound such as (2-iodoethynyl)trimethylsilane, (2-iodoethynyl)triethyisilane, (2-iodoethynyl)-t-butyldimethylsilane, or (2-iodoethynyl)triisopropyisilane, more preferably (2-bromoethynyl)trimethylsilane.

In the coupling reaction between the alkenylmagnesium halide compound prepared from the haloalkene compound (1) and the alkyne compound (2), an amount of the haloalkene compound (1) is preferably from 0.8 g to 1.4 mol per mol of the alkyne compound (2) in view of the completion of the reaction and the economy.

In the coupling reaction, a catalyst may be used in view of the reactivity if necessary.

Examples of the catalyst used in the coupling reaction include monovalent copper halides such as copper (I) chloride, copper (I) bromide, and copper (I) iodide, divalent copper halides such as copper (I) cyanide, copper (I) oxide, copper (II) chloride, copper (II) bromide, and copper (II) iodide, and four-coordinate complexes (complex compounds) of copper such as dilithium tetrachlorocuprate. Additional examples include copper (II) cyanide and copper (II) oxide. In view of the reactivity, halogen four-coordinate complexes of copper such as dilithium tetrachlorocuprate are preferred. These catalysts may be used either alone or in combination thereof. The catalyst may be commercially available one.

An amount of the catalyst is preferably from 0.003 to 0.300 mol, more preferably from 0.003 to 0.030 mol, per mol of the alkyne compound (2) in view of the economy.

Examples of a solvent used in the coupling reaction include ether solvents such as tetrahydrofuran, diethyl ether, and 4-methyltetrahydropyran and hydrocarbon solvents such as toluene, xylene, and hexane. Tetrahydrofuran is preferred among these in view of the reactivity. The solvent may be used either alone or in combination thereof. The solvent may be commercially available one.

An amount of the solvent is preferably from 50 to 800 g per mol of the alkyne compound (2) in view of the reactivity.

A reaction temperature in the coupling reaction is preferably from 0 to 50° C. in view of the reactivity. A reaction time in the coupling reaction differs, depending on a production scale, and is preferably 0.1 to 20 hours in view of the reactivity.

A silane compound of formula (3) is obtained by the coupling reaction between the alkenylmagnesium halide compound prepared from the haloalkene compound (1) and the alkyne compound (2). Examples of a geometric isomer of the silane compound (3) in —$CR^1$=$CR^2$-include E isomers and Z isomers. Examples of the silane compound (3) include 5-octen-1-ynyltrialkylsilane compounds such as (5Z)-5-octen-1-ynyltrimethylsilane and (5E)-5-octen-1-ynyltrimethylsilane; 5-decen-1-ynyltrialkylsilane compounds such as (5E)-5-decen-1-ynltrimethysilane; 5-hexadecen-1-ynyltrialkylsilane compounds such as (5Z)-5-hexadecen-1-ynyltrimethylsilane; and 8-[(tetrahydro-2H-pyran-2-yl)oxy]-5-octen-1-ynyltrialkylsilane compounds such as (5Z)-8-[(tetrahydro-2H-pyran-2-yl)oxy]-5-octen-1-ynyltrimethylsilane. The silane compound (3) having a trimethylsilyl group as the silyl group, Si($R^3$)($R^4$)($R^5$), is preferred in view of the easiness of the desilylation reaction.

Next, the step of obtaining a 5-alken-1-yne compound of the following formula (4) by a desilylation reaction of the silane compound of formula (3) in the process for preparing the 5-alken-1-yne compound will be described hereinafter.

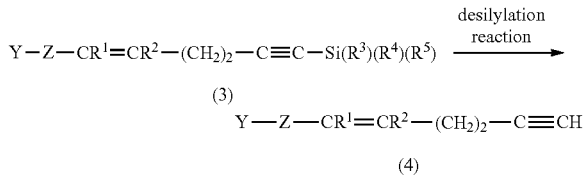

$$Y-Z-CR^1=CR^2-(CH_2)_2-C\equiv C-Si(R^3)(R^4)(R^5) \xrightarrow{\text{desilylation reaction}}$$

(3)

$$Y-Z-CR^1=CR^2-(CH_2)_2-C\equiv CH$$

(4)

The desilylation reaction is carried out using, for example, a desilylating agent and, if necessary, a solvent.

Examples of the desilylating agent include inorganic bases, metal alkoxides, and fluorides. These desilylating agents may be used either alone or in combination thereof. The desilylating agent may be commercially available one.

Examples of the inorganic bases include alkali metal hydroxides such as lithium hydroxide, sodium hydroxide, and potassium hydroxide. Additional examples of it include potassium carbonate and cesium carbonate. These inorganic bases may be used as an aqueous solution thereof. For example, an aqueous sodium hydroxide solution preferably has a concentration of from 10 to 40 wt %, more preferably from 20 to 30 wt % in view of the reactivity.

Examples of the metal alkoxides include sodium t-butoxide, potassium t-butoxide, sodium methoxide, potassium methoxide, sodium ethoxide, potassium ethoxide, sodium trimethylsilyloxide, and potassium trimethylsilyloxide.

Examples of the fluorides include hydrogen fluoride pyridine, potassium fluoride, cesium fluoride, and tetra-n-butylammonium fluoride.

As the desilylating agent, an aqueous solution of an alkali metal hydroxide such as aqueous solution of sodium hydroxide, and potassium trimethylsilyloxide are preferred in view of the reactivity.

An amount of the desilylating agent is preferably from 1.0 to 10.0 mol, more preferably from 1.0 to 5.0 mol, per mol of the silane compound (3) in view of the reactivity and the economy.

Examples of a solvent used, if necessary, in the desilylation reaction include aprotic polar solvents such as N,N-dimethylformamide, N,N-dimethylacetamide, N,N-dimethylpropionamide, 1,3-dimethyl-2-imidazolidinone dimethyl sulfoxide, and hexamethylphosphoric triamide; ether solvents such as tetrahydrofuran, diethyl ether, and 4-methyltetrahydropyran; primary alcohols having from 1 to 4 carbon atoms such as methanol, ethanol, 1-propanol, and 1-butanol; secondary alcohols such as isopropyl alcohol: and tertiary alcohols such as t-butyl alcohol. The solvent may be commercially available one. The solvent may be used either alone or in combination thereof.

The optimum solvent differs, depending on a desilylating agent used. For example, in view of the reactivity, methanol is preferred when an aqueous sodium hydroxide solution is used; dimethyl sulfoxide is preferred when potassium trimethylsilyloxide is used; and tetrahydrofuran is preferred when tetra-n-butylammonium fluoride is used.

An amount of the solvent used, if necessary, in the desilylation reaction is preferably from 0 to 3000 g per mol of the silane compound (3) in view of the reactivity.

A reaction temperature in the desilylation reaction differs, depending on a solvent used, and is preferably 0 to 150° C., more preferably 25 to 80° C., in view of the reactivity and the yield. A reaction time in the desilylation reaction differs, depending on a solvent used or a production scale, and is preferably 1 to 50 hours in view of the reactivity.

When the silane compound (3) is used in the desilylation reaction without being purified it, the desilylating agent and solvent may be used in the aforesaid amounts, respectively, per mol of the alkyne compound (2).

By the desilylation reaction of the silane compound (3), a 5-alken-1-yne compound (4) is obtained. A geometric isomer of —CR$^1$═CR$^2$— in the 5-alken-1-yne compound (4) includes an E isomer and a Z isomer. Examples of the 5-alken-1-yne compound (4) include 5-octen-1-yne compounds such as (5Z)-5-octen-1-yne and (5E)-5-octen-1-yne, 5-decen-1-yne compounds such as (5E)-5-decen-1-yne, 5-hexadecen-1-yne compounds such as (5Z)-5-hexadecen-1-yne, and 8-[(tetrahydro-2H-pyran-2-yl)oxy]-5-octen-1-yne compounds such as (5Z)-8-[(tetrahydro-2H-pyran-2-yl)oxy]-5-octen-1-yne.

A 5-octen-1-yne compound of the following formula (4-2) as an example of the 5-alken-1-yne compound (4) is prepared by a step of subjecting (i) a 3-hexenylmagnesium halide compound prepared from a 1-halo-3-hexene compound of the following formula (1-2) and (ii) the alkyne compound of the following formula (2) to a coupling reaction to form a silane compound of the following formula (3-2) and a step of subjecting the resulting silane compound to a desilylation reaction to form the 5-octen-1-yne compound of the following formula (4-2).

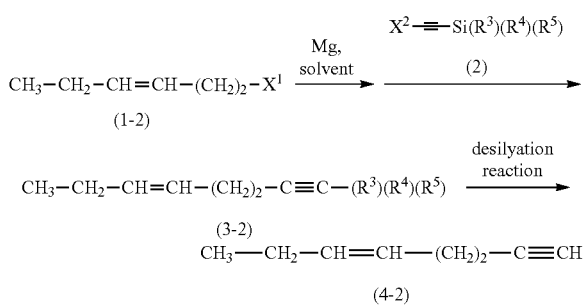

A 5-decen-1-yne compound of the following formula (4-3) as another example of the 5-alken-1-yne compound is prepared by a step of subjecting (i) a 3-octenylmagnesium halide compound prepared from a 1-halo-3-octene compound of the following formula (1-3) and (ii) the alkyne compound of the following formula (2) to coupling reaction to form a silane compound of the following formula (3-3) and a step of subjecting the resulting silane compound to a desilylation reaction to form the 5-decen-1-yne compound of the following formula (4-3).

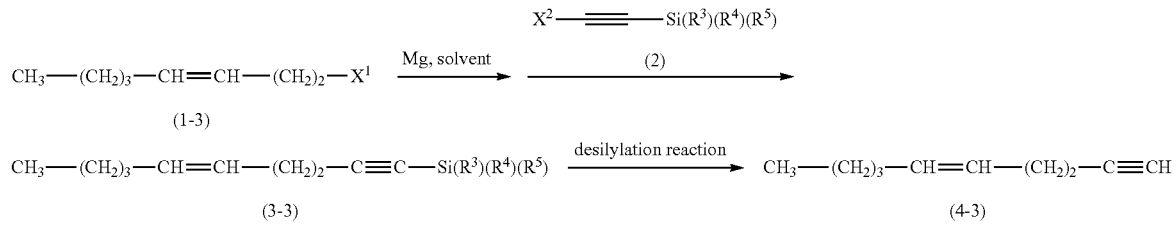

A 5-hexadecen-1-yne compound of the following formula (4-4) as a further example of the 5-alken-1-yne compound is prepared by a step of subjecting (i) a 3-tetradecenylmagnesium halide compound prepared from a 1-halo-3-tetradecene compound of the following formula (1-4) and (ii) the alkyne compound of the following formula (2) to a coupling reaction o form a silane compound of the following formula (3-4) and a step of subjecting the resulting silane compound to a desilylation reaction to form the 5-hexadecen-1-yne compound of the following formula (4-4).

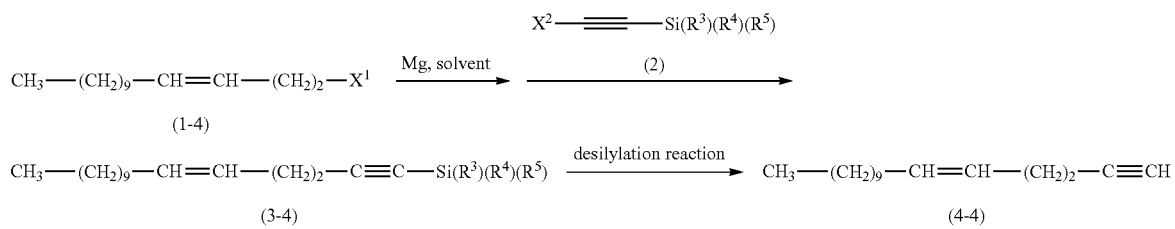

A 8-[(tetrahydro-2H-pyran-2-yl)oxy]-5-octen-1-yne compound of the following formula (4-5) as a still further example of the 5-alken-1-yne compound is prepared by a step of subjecting (i) a 6-[(tetrahydro-2H-pyran-2-yl)oxy]-3-hexenylmagnesium halide compound prepared from a 1-halo-6-[(tetrahydro-2H-pyran-2-yl)oxy]-3-hexene compound of the following formula (1-5) and (ii) the alkyne compound of the following formula (2) to a coupling reaction to form a silane compound of the following formula (3-5) and a step of subjecting the resulting silane compound to a desilylation reaction to form a 8-[(tetrahydro-2H-pyran-2-yl)oxy]-5-octen-1-yne compound of the following formula (4-5).

-continued

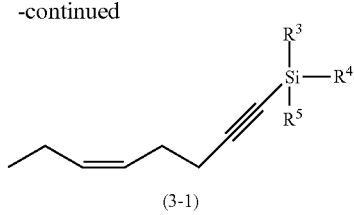

Next, will be explained a step of subjecting the resulting silane compound of the following formula (3-1) to a desilylation reaction to form (5Z)-5-octen-1-yne of the following formula (4-1) in the process for preparing a (6Z)-1,1-

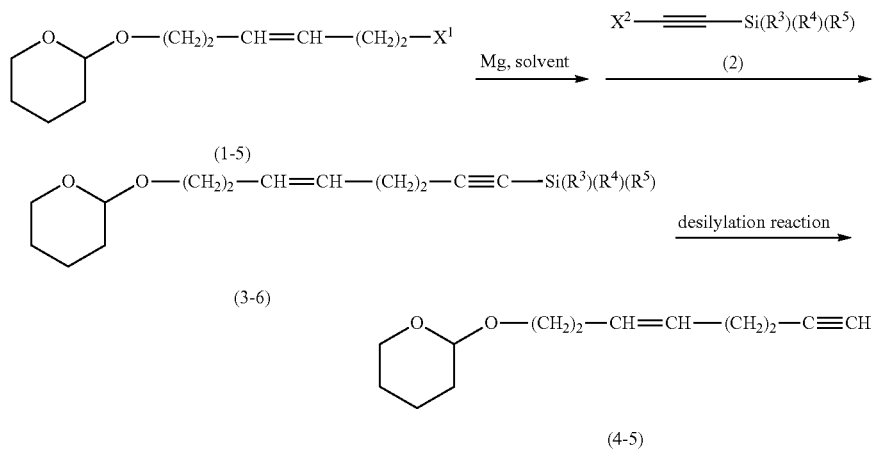

Next, will be explained a step of subjecting (i) a (3Z)-3-hexenylmagnesium halide compound prepared from a (3Z)-1-halo-3-hexene compound of the following formula (1-1) and (ii) the alkyne compound of the following formula (2) to a coupling reaction to form a slime compound of the following formula (3-1) in the process for preparing a (6Z)-1,1-dialkoxy-6-nonen-2-yne compound.

$X^1$ in formula (1-1) and the alkyne compound (2) are the same as those described above and the coupling reaction may be carried out in similar reaction conditions as described above.

dialkoxy-6-nonen-2-yne compound. The desilylation reaction may be carried out in similar reaction conditions as described above.

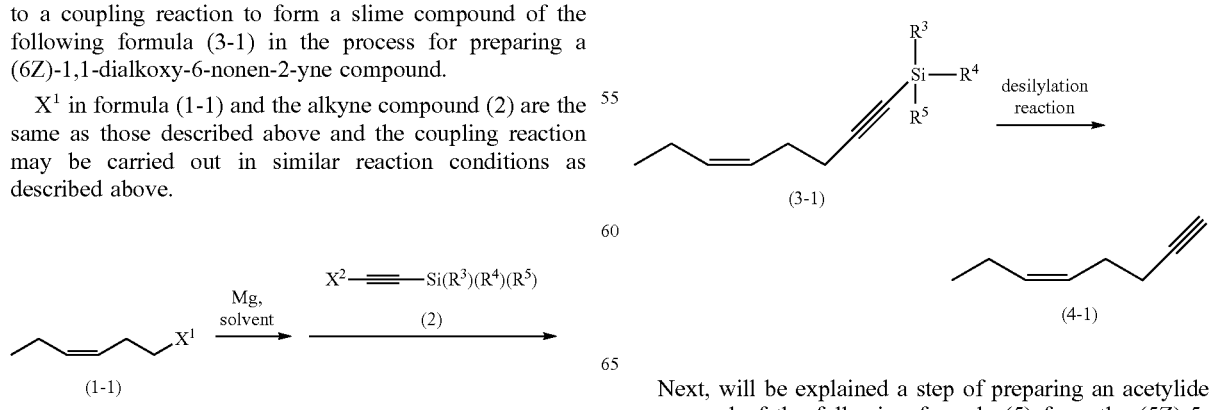

Next, will be explained a step of preparing an acetylide compound of the following formula (5) from the (5Z)-5- octen-1-yne of the following formula (4-1) in the process for preparing a (6Z)-1,1-dialkoxy-6-nonen-2-yne compound.

M in formula (5) represents Li, Na, K, or MgX³. X³ represents a halogen atom and examples of it are the same as those for X¹.

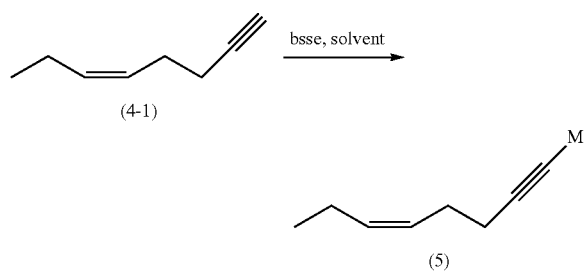

The acetylide compound (5) prepared from the (5Z)-5-octen-1-yne (4-1) may be obtained by reacting the (5Z)-5-octen-1-yne (4-1) with a base in a solvent.

Examples of the base used in preparing the acetylide compound (5) include Grignard reagents such as methylmagnesium chloride, methylmagnesium bromide, ethylmagnesium chloride, ethylmagnesium bromide, isopropylmagnesium chloride, and n-butylmagnesium chloride; metal alkoxides such as sodium t-butoxide, potassium t-butoxide, sodium methoxide, potassium methoxide, sodium ethoxide, and potassium ethoxide; metal hydrides such as lithium hydride and sodium hydride; alkyl lithiums such as methyl lithium, n-butyllithium, and t-butyllithium; alkynyl lithiums such as sodium acetylide; and metal amides such as lithium amide, lithium diisopropylamide, and sodium bis(trimethylsilyl)amide. These bases used in preparing the acetylide compound (5) may be used either alone or in combination thereof. The base used in preparing the acetylide compound (5) may be commercially available one.

As the base used in preparing the acetylide compound (5), the Grignard reagents are preferred, with alkylmagnesium halides having from 1 to 5 carbon atoms such as methylmagnesium chloride being more preferred, in view of the reactivity and the economy.

An amount of the base used in preparing the acetylide compound (5) is preferably from 1.0 to 5.0 mol, more preferably from 1.0 to 3.0 mol, per mol of the (5Z)-5-octen-1-yne (4-1), in view of the reactivity and the economy.

The solvent used for the preparation of the acetylide compound (5) differs, depending on a base used, and may be aprotic polar solvents such as N,N-dimethylformamide, N,N-dimethylacetamide, N,N-dimethylpropionamide, 1,3-dimethyl-2-imidazolidinone, dimethyl sulfoxide, and hexamethylphosphoric triamide; ether solvents such as tetrahydrofuran diethyl ether, and 4-methyltetrahydropyran; and hydrocarbon solvents such as toluene, xylene, and hexane. Tetrahydrofuran is preferred in view of the reactivity. The solvent may be used either alone or in combination thereof. The solvent may be commercially available one.

An amount of the solvent differs, depending on a production scale, and is preferably from 10 to 500 g per mol of the (5Z)-5-octen-1-yne (4-1) in view of the reaction rate.

A reaction temperature in preparing the acetylide compound (5) differs, depending on u solvent used, and is preferably −78 to 100° C. in view of the reactivity. A reaction time in preparing the acetylide compound (5) differs, depending on a solvent used or a production scale, and is preferably 0.1 to 30 hours in view of the reaction rate.

Examples of the acetylide compound (5) include (5Z)-5-octen-1-ynyl alkali metal compounds such as (5Z)-5-octen-1-ynyl lithium, (5Z)-5-octen-1-ynyl sodium, and (5Z)-5-octen-1-ynyl potassium; and (5Z)-5-octen-1-ynylmagnesium halide compounds such as (5Z)-5-octen-1-ynylmagnesium chloride.

Next, will be explained a step of subjecting the acetylide compound of the following formula (5) and an orthoformic acid ester compound of the following formula (6) to a nucleophilic substitution reaction to form a (6Z)-1,1-dialkoxy-6-nonen-2-yne compound of the following formula (7a) in the process for preparing a (6Z)-1,1-dialkoxy-6-nonen-2-yne compound.

Three R⁶s in formula (6) for the orthoformic acid ester compound may be the same or different at each occurrence and each independently represent a monovalent hydrocarbon group having front 1 to 6 carbon atoms, preferably from 1 to 3 carbon atoms. Examples of the monovalent hydrocarbon group, R⁶, are the same as the monovalent hydrocarbon group, R¹ or R². These three R⁶s are preferably the same with each other in view of the easy availability and purification after the reaction.

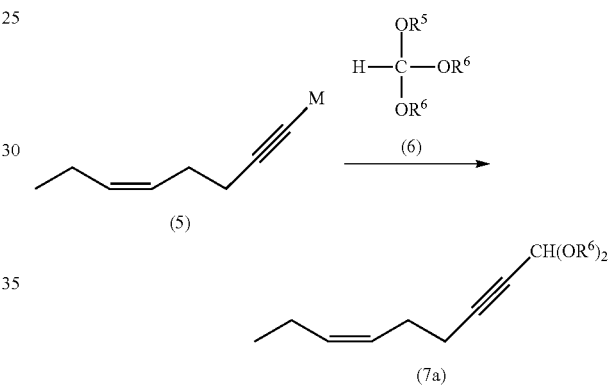

Examples of the orthoformic acid ester compound (6) include orthoformic acid ester compounds having a linear alkyl group such as methyl orthoformate, ethyl orthoformate, propyl orthoformate, butyl orthoformate, pentyl orthoformate, and hexyl orthoformate; and orthoformic acid ester compounds having a branched alkyl group such as isopropyl orthoformate. Methyl orthoformate and ethyl orthoformate are preferred in view of the easy availability. The orthoformic acid ester compound (6) may be commercially available or may be synthesized in house.

An amount of the orthoformic acid ester compound (6) is preferably from 1.0 to 3.0 mol per mol of the acetylide compound (5) in view of the reactivity.

The kind and the amount of the solvent in the nucleophilic substitution reaction between the acetylide compound (5) and the orthoformic acid ester compound (6) may be same as or different from the kind and the amount of the solvent used in preparing the acetylide compound (5).

A reaction temperature in the nucleophilic substitution reaction is preferably from 75 to 130° C. to allow the reaction to proceed smoothly and prevent evaporation of the solvent. A reaction time in the nucleophilic substitution reaction differs, depending on a solvent used or a production scale, and is preferably 3 to 35 hours in view of the reactivity.

A (6Z)-1,1-dialkoxy-6-nonen-2-yne compound of formula (7a) is obtained by the nucleophilic substitution reaction between the acetylide compound (5) and the orthoformic acid ester compound (6). $R^6$ in the (6Z)-1,1-dialkoxy-6-nonen-2-yne compound (7a) is the same as $R^6$ in the orthoformic acid ester compound (6).

Examples of the (6Z)-1,1-dialkoxy-6-nonen-2-yne compound (7a) include (6Z)-1,1-dimethoxy-6-nonen-2-yne, (6Z)-1,1-diethoxy-6-nonen-2-yne, (6Z)-1,1-dipropoxy-6-nonen-2-yne, and (6Z)-1,1-diisopropoxy-6-nonen-2-yne. (6Z)-1,1-dimethoxy-6-nonen-2-yne and (6Z)-1,1-diethoxy-6-nonen-2-yne are preferred in view of easy production.

A (6E)-1,1-dialkoxy-6-nonen-2-yne compound of the following formula (7b) may be prepared by using, as the haloalkene compound (1), an E form of a 1-halo-3-hexene compound. $R^6$ in the (6E)-1,1-dialkoxy-6-nonen-2-yne compound (7-2) is the same as $R^6$ in the orthoformic acid ester (6).

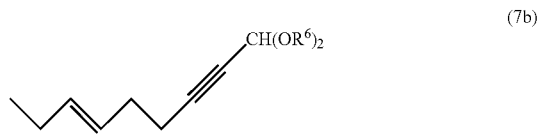

(7b)

Examples of the (6E)-1,1-dialkoxy-6-nonen-2-yne compound (7-2) include (6E)-1,1-dimethoxy-6-nonen-2-yne, (6E)-1,1-diethoxy-6-nonen-2-yne, (6E)-1,1-dipropoxy-6-nonen-2-yne, and (6E)-1,1-diisopropoxy-6-nonen-2-yne.

Next, will be explained a step of subjecting the (6Z)-1,1-dialkoxy-6-nonen-2-yne compound of the following formula (7a) to a reduction reaction to form a (6Z)-1,1-dialkoxy-2,6-nonadiene compound of the following formula (8) in the process for preparing a (2E,6Z)-2,6-nonadienal.

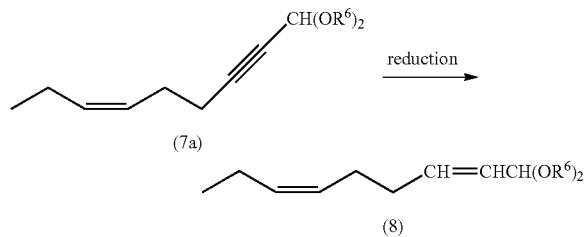

Examples of the reduction include a catalytic reduction (catalytic hydrogenation); a reduction with potassium hydroxide and N,N-dimethylformamide (DMF) in the presence of a palladium catalyst such as palladium acetate; a reduction using zinc in an alcohol solvent; a Birch reduction; a reduction comprising hydroxylation to obtain vinyl silan and then desilylation of the resulting vinylsilane; and a reduction comprising hydroboration with a dialkylborane and protonation subsequent thereto. The catalytic reduction is preferred in view of the selectivity and the productivity.

The catalytic reduction is carried out by adding a hydrogen gas in the presence of a metal catalyst. Examples of the metal catalyst used in the catalytic reduction include palladium catalysts such as Lindlar catalyst, palladium carbon, Pd-PEI obtained by poisoning palladium carbon with a polyethyleneimine polymer (PEI), and palladium hydroxide; nickel catalysts such as nickel boride and P-2 nickel boride catalyst (Thomas J. Caggiano et al. Encyclopedia of Reagents for Organic Synthesis: 3694-3699) (which catalyst may hereinafter be called "P2-Ni catalyst"); and platinum catalysts such as Adams catalyst. The Lindlar catalyst and the nickel catalysts are preferred in view of the economy. A catalyst in solid form may be dispersed in a solvent.

An amount of the metal catalyst differs among the catalysts. When the catalyst is in solid form, such as the Lindlar catalyst, it is used preferably in an amount of from 0.01 to 50.00 g per mol of the (6Z)-1,1-dialkoxy-6-nonen-2-yne compound (7a) in view of the reactivity. On the other hand, the P2-Ni catalyst is used preferably in an amount of from 0.001 to 0.500 mol nickel compound per mol of the (6Z)-1,1-dialkoxy-6-nonen-2-yne compound (7a).

When the metal catalyst has too much high activity, a catalytic poison may be used if necessary. Examples of the catalytic poison used in the catalytic reduction include amine compounds such as pyridine, quinoline, and ethylenediamine and sulfur compounds such as benzenethiol, diphenyl sulfide, dimethyl sulfide, and dimethyl sulfoxide.

An amount of the catalytic poison differs largely among catalytic poisons, and are preferably 0.0001 to 10.0000 g per mol of the (6Z)-1,1-dialkoxy-6-nonen-2-yne compound (7a) in view of the reaction rate and the geometric selectivity.

Examples of the catalyst used for the catalytic reduction include polar solvents such as acetonitrile, methyl acetate, and ethyl acetate; hydrocarbon solvents such as toluene, pentane, hexane, heptane, cyclohexane, and cyclohexane; and alcohol solvents such as methanol, ethanol, 1-propanol, 1-butanol, 1-pentanol, 1-hexanol, 2-propanol, 2-butanol, and cyclohexanol. The solvent may be used either alone or in combination thereof. The solvent may be commercially available one.

A preferred solvent in the catalytic reduction is an alcohol solvent such as methanol, ethanol, 1-propanol, 1-butanol, or 2-propanol for the nickel catalyst; a hydrocarbon solvent such as hexane for the Lindlar catalyst; and a polar solvent such as methyl acetate or ethyl acetate for the palladium catalyst such as palladium carbon, in view of the reactivity.

An amount of the solvent differs, depending on a catalyst and a solvent used, and is preferably 0 to 1000 g per mol of the (6Z)-1,1-dialkoxy-6-nonen-2-yne compound (7a) in view of the reactivity.

A reaction temperature in the catalytic reduction differs, depending on the kind of the catalyst and solvent used, and is preferably 40 to 160° C. in view of the geometric selectivity. A reaction time of the catalytic reduction is preferably from 1 to 50 hours in view of the yield.

Examples of the geometric isomer of the (6Z)-1,1-dialkoxy-2,6-nonadiene compound (8) obtained by the reduction of the (6Z)-1,1-dialkoxy-6-nonen-2-yne compound (7a) include (2E,6Z)-1,1-dialkoxy-2,6-nonadiene compounds and (2Z,6Z)-1,1-dialkoxy-2,6-nonadiene compounds.

Examples of the (2E,6Z)-1,1-dialkoxy-2,6-nonadiene compounds include (2E,6Z)-1,1-dimethoxy-2,6-nonadiene and (2E,6Z)-1,1-diethoxy-2,6-nonadiene.

Examples of the (2Z,6Z)-1,1-dialkoxy-2,6-nonadiene compounds include (2Z,6Z)-1,1-dimethoxy-2,6-nonadiene and (2Z,6Z)-1,1-diethoxy-2,6-nonadiene.

Since (2E,6Z)-2,6-nonadienal (9) can be prepared convergently by a hydrolysis described hereinafter, one of the geometrical isomers may be selectively prepared. Alternatively, a mixture of geometric isomers may be prepared by the reduction.

Next, will be explained a step of hydrolyzing the (6Z)-1,1-dialkoxy-2,6-nonadiene compound of the following formula (8) to form (2E,6Z)-2,6-nonadienal of the following formula (9) in the process for preparing (2E,6Z)-2,6-nonadienal.

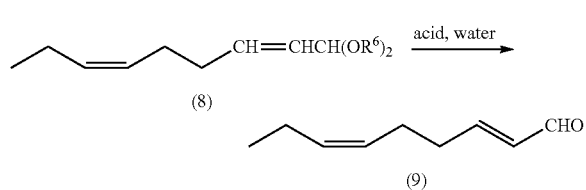

(8) → (9)

The hydrolysis is carried out using, for example, an acid and water and, if necessary, a solvent.

Examples of the acid used for the hydrolysis include inorganic acids such as hydrochloric acid, hydrobromic acid, nitric acid, and sulfuric acid, p-toluenesulfonic acid, trifluoroacetic acid, acetic acid, formic acid, oxalic acid, iodotrimethylsilane, and titanium tetrachloride. Hydrochloric acid is preferred in view of the reactivity. These acids may be used either alone or in combination thereof. The acid may be commercially available one.

An amount of the acid is preferably from 0.01 to 15.00 mol per mol of the (6Z)-1,1-dialkoxy-2,6-nonadiene compound (8) in view of the reactivity.

An amount of water used for the hydrolysis is preferably from 18 to 3000 g per mol of the (6Z)-1,1-dialkoxy-2,6-nonadiene compound (8) in view of the reactivity.

Examples of the solvent used in the hydrolysis include ether solvents such as tetrahydrofuran, diethyl ether, and 4-methyltetrahydropyran, hydrocarbon solvents such as toluene, xylene, and hexane, polar solvents such as N,N-dimethylformamide, N,N-dimethylacetamide, acetonitrile, dichloromethane, and chloroform, and alcohol solvents such as methanol and ethanol. The solvent may be used either alone or in combination thereof. The solvent may be commercially available one.

The optimum solvent differs, depending on an acid used. When hydrochloric acid is used as the acid, no solvent or the hydrocarbon solvent such, as hexane is preferably used in view of the reactivity.

An amount of the solvent is preferably from 0 to 3000 g per mol of the (6Z)-1,1-dialkoxy-2,6-nonadiene compound (8) in view of the reactivity.

A reaction temperature in the hydrolysis differs, depending on a solvent used, and is preferably −20 to 150° C. in view of the reactivity. A reaction time in the hydrolysis differs, depending on a solvent used or a production scale, and is preferably 0.5 to 10 hours in view of the reactivity.

A pH of the aqueous solution in the hydrolysis system is preferably 1.0 or less, more preferably from −1.0 to +1.0, in order to proceed sufficiently with the isomerization to thereby E-selectively obtain (2E,6Z)-2,6-nonadienal (9) with a high geometric purity. The pH may be determined by, for example, a pH test strip or a pH meter after adjusting the temperature of the object at 25° C.

According to the aforesaid manner, the olefinic moiety at position 2 of the (6Z)-1,1-dialkoxy-2,6-nonadiene compound converges substantially 100% into an E form by the isomerization of a conjugated aldehyde formed by the hydrolysis. Even when the olefinic moiety at position 2 rearranges into the olefinic moiety at position 3 under the influence by the acetal structure in the hydrolysis, it converges into a more stable conjugated aldehyde of an E form, so that high-purity (2E,6Z)-2,6-nonadienal (9) can be obtained. The E form may be selectively prepared in the olefinic moiety at position 2 of (2E,6Z)-2,6-nonadienal (9) by the isomerization of the conjugated aldehyde, so that this is a very industrially useful production method.

Next, will be explained a step of epoxidizing (2E,6Z)-2,6-nonadienal of the following formula (9) and a peroxide to form (2E)-cis-6,7-epoxy-2-nonenal of the following formula (10) in the process for preparing (2E)-cis-6,7-epoxy-2-nonenal.

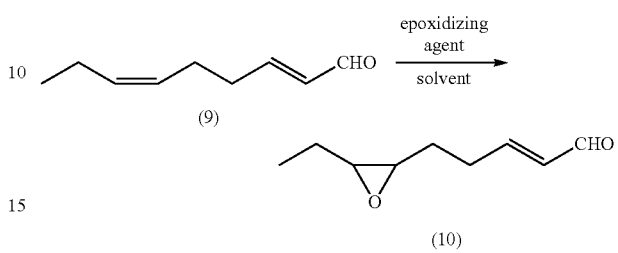

(9) → (10)

The epoxidation of (2E,6Z)-2,6-nonadienal (9) may be carried out, for example, by reacting it with an epoxidizing agent in a solvent.

Examples of the epoxidizing agent used for the epoxidation include percarboxylic acid compounds having from 1 to 7 carbon atoms such as meta-chloroperbenzoic acid (MCPBA), performic acid, and peracetic acid, and dioxirane compounds such as dimethyldioxirane and methyltrifluoromethyldioxirane. Meta-chloroperbenzoic acid is preferred in view of the handling. These epoxidizing agents may be used either alone or in combination thereof. The epoxidizing agent may be commercially available one.

An amount of the epoxidizing agent is preferably front 1.0 to 2.0 mol per mol of (2E,6Z)-2,6-nonadienal (9) in view of the reactivity.

It is also possible to cause asymmetric epoxidation in the conditions of the Jacobsen-Katsuki epoxidation reaction or the conditions of the Shi asymmetric epoxidation reaction.

When the percarboxylic acid compound is used as the epoxidizing agent, an alkali metal hydrogen carbonate such as sodium hydrogen carbonate may further be used, if necessary, in order to prevent acidification of the reaction system caused by a carboxylic acid compound derived from the percarboxylic acid compound.

Examples of the solvent used in the epoxidation include hydrocarbon solvents such as toluene and hexane, ether solvents such as tetrahydrofuran, 4-methyltetrahydropyran and diethyl ether and polar solvents such as dichloromethane and acetonitrile. The solvent may be used either alone or in combination thereof. The solvent may be commercially available one.

The optimum solvent differs among the epoxidizing agents. For example, a polar solvent such as dichloromethane is preferred in view of the reactivity when meta-chloroperbenzoic acid is used as the epoxidizing agent.

An amount of the solvent is preferably from 100 to 8000 g per mol of (2E,6Z)-2,6-nonadienal (9) in view of the reactivity.

A reaction temperature in the epoxidation differs, depending on a solvent used, and is preferably from −30 to 50° C. in view of the reactivity. A reaction time in the epoxidation differs, depending on a solvent used or a production scale, and is preferably from 1 to 30 hours in view of productivity.

Examples of (2E)-cis-6,7-epoxy-2-nonenal (10) obtained by the epoxidation of (2E,6Z)-2,6-nonadienal (9) with the peroxide include (2E,6R,7S)-6,7-epoxy-2-nonenal of the following formula (10-1) and (2E,6S,7R)-6,7-epoxy-2-nonenal of the following formula (10-2) and raccmates and scalemic mixtures thereof. The double bond between the α-carbon and the β-carbon of the carbonyl group in (2E, 6Z)-2,6-nonadienal is conjugated with a formyl group and, accordingly, has a low electron density and, subsequently, is less susceptible to epoxidation, so that epoxidation of (2E, 6Z)-2,6-nonadienal (9) is a preferable choice for preparing (2E)-cis-6,7-epoxy-2-nonenal (10).

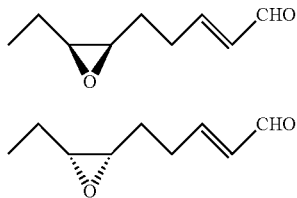

(10-1)

(10-2)

EXAMPLES

The present invention will be further described with reference to the following Examples. It should be construed that the invention is not limited to or by the Examples. The term "crude yield" as used herein means a yield of a crude product without being purified.

Example 1

<Preparation of (5Z)-5-octen-1-yne (4-1)>

Magnesium (2.43 g, 0.100 gram atoms) and tetrahydrofuran (9.43 g) were added to a reactor and stirred at from 60 to 65° C. for 30 minutes. Then, (3Z)-1-chloro-3-hexene (1-1: $X^1$=Cl) (11.3 g, 0.0952 mol) was added dropwise at from 60 to 70° C. and the reaction mixture was stirred at from 70 to 75° C. for 6 hours to form (3Z)-3-hexenylmagnesium chloride. Next, dilithium tetrachlorocuprate (0.24 g, 0.0011 mol), (2-bromoethynyl)trimethylsilane (14.0 g, 0.0793 mol), and tetrahydrofuran (7.86 g) were added to another reactor and stirred at from 5 to 10° C. for 10 minutes. Then, the aforesaid solution of (3Z)-3-hexenylmagnesium chloride in tetrahydrofuran was added dropwise at from 30 to 35° C. After completion of the dropwise addition, the stirring was continued for one hour and then at from 30 to 35° C. Then, ammonium chloride (1.97 g), an aqueous 20 wt % hydrogen chloride (3.18 g), and water (120 g) were added to the reaction mixture to terminate the reaction. After phase separation of the resulting mixture and removal of the aqueous layer thus obtained, the organic layer containing (5Z)-5-octen-1-ynyltrimethylsilane was washed with an aqueous 2 wt % ammonia (120 g). Next, the organic layer containing (5Z)-5-octen-1-ynyltrimethylsilane obtained above, an aqueous 25 wt % sodium hydroxide solution (38.1 g), and methanol (79.3 g) were added to another reactor and stirred at from 40 to 45° C. for 3 hours. After phase separation of the resulting mixture and removal of the aqueous layer thus obtained, the organic layer was concentrated in a reduced pressure and the residue was subjected to distillation in a reduced pressure to obtain (5Z)-5-octen-1-yne (4-1) (7.89 g, 0.0730 mol) in a yield of 92.0%.

(5Z)-5-Octen-1-yne (4-1)

[Nuclear magnetic resonance spectrum] $^1$H-NMR (500 MHz, CDCl$_3$): δ 0.96 (3H, t, J=7.7 Hz), 1.94 (1H, t, J=2.7 Hz), 2.05 (2H, qd, J=7.7, 7.71 Hz), 2.20-2.23 (2H, m), 2.25-2.27 (2H, m), 5.30-5.39 (1H, m), 5.43-5.56 (1H, m); $^{13}$C-NMR (7.5.6 MHz, CDCl$_3$): 14.27, 18.84, 20.56, 26.23, 68.23, 84.16, 126.77, 133.22

[Mass spectrum] EI-Mass spectrum (70 eV): m/z 108(M+), 93, 79, 69, 53, 41, 27

[Infrared absorption spectrum] (NaCl): νmax 3308, 3010, 2964, 2934, 2875, 2119, 1655, 1456, 1375, 1253, 1117, 846, 715, 633

Example 2

<Preparation of (5E)-5-decen-1-yne (4-3)>

Magnesium (2.45 g, 0.101 gram atoms) and tetrahydrofuran (9.51 g) were added to a reactor and stirred at from 60 to 65° C. for 30 minutes. Then, (3E)-1-chloro-3-octene (1-3:$X^1$=Cl) (14.1 g, 0.0960 mol) was added dropwise at from 60 to 70° C. and the reaction mixture was stirred at from 70 to 75° C. for 4 hours to form (3Z)-3-octenylmagnesium chloride. Next, dilithitun tetrachlorocuprate (0.24 g, 0.0011 mol), (2-bromoethynyl)trimethylsilane (14.2 g, 0.0800 mol), and tetrahydrofuran (7.93 g) were added to another reactor and stirred at from 5 to 10° C. for 10 minutes. Then, the aforesaid solution of the (3Z)-3-octenylmagnesium chloride in tetrahydrofuran was added dropwise at from 30 to 35° C. After completion of the dropwise addition, the reaction mixture was stirred at from 30 to 35° C. for one hour and then, the reaction was terminated by adding thereto ammonium chloride (1.97 g), an aqueous 20 wt % hydrogen chloride (3.18 g), and water (120 g). After phase separation of the resulting mixture and removal of the aqueous layer thus obtained, the organic layer containing the (5E)-5-decen-1-ynyltrimethylsilane was washed with an aqueous 2 wt % ammonia (120 g). Next, the organic layer containing the (5E)-5-decen-1-ynyltrimethylsilane obtained above, an aqueous 25 wt % sodium hydroxide solution (38.4 g) and methanol (80.0 g) were added to another reactor and stirred at from 40 to 45° C. for 2 hours. After phase separation of the reaction mixture and removal of the aqueous layer thus obtained, the organic layer was concentrated in a reduced pressure and the residue was subjected to distillation in a reduced pressure to obtain (5E)-5-decen-1-yne (4-3) (9.39 g, 0.0689 mol) in a yield of 86.2%.

(5E)-5-Decen-1-yne (4.3)

[Nuclear magnetic resonance spectrum] $^1$H-NMR (500 MHz, CDCl$_3$): δ 0.88 (3H, t, J=7.3 Hz), 1.26-1.37 (4H, m), 1.94 (1H, t, J=2.7 Hz), 1.99 (2H, td, J=6.9, 6.9 Hz), 2.18-2.27 (4H, m), 5.34-5.52 (2H, m); $^{13}$C-NMR (75.6 MHz, CDCl$_3$): 13.91, 18.92, 22.15, 31.60 (2C), 32.17, 68.32, 84.20, 127.87, 132.06

[Mass spectrum] EI-Mass spectrum (70 eV): m/z 136 (M+), 121, 107, 93, 79, 67, 55, 41, 27

[Infrared absorption spectrum] (NaCl): νmax 3312, 2958, 2926, 2873, 2855, 2120, 1466, 1435, 1379, 1244, 968, 731, 631

Example 3

<Preparation of (5Z)-5-hexadecen-1-yne (4-4)>

Magnesium (2.45 g, 0.101 gram atoms) and tetrahydrofuran (9.51 g) were added to a reactor and stirred at from 60 to 65° C. for 30 minutes. Then, (3Z)-1-chloro-3-tetradecene (1-4:$X^1$=Cl) (22.2 g, 0.0960 mol) was added dropwise at from 60° C. to 70° C. and the reaction mixture was stirred at from 70 to 75° C. for 4 hours to form (3Z)-3-tetradecenylmagnesium chloride. Next, dilithium tetrachlorocuprate (0.24 g, 0.0011 mol), (2-bromoethynyl)trimethylsilane (14.2 g, 0.0800 mol), and tetrahydrofuran (7.93 g) were added to another reactor and stirred at from 5 to 10° C. for 10 minutes. Then, the aforesaid solution of the (3Z)-3-tetradecenylmagnesium chloride in tetrahydrofuran was added dropwise at from 30 to 35° C. After completion of the dropwise addition, the reaction mixture was stirred at from 30 to 35° C. for one hour and then, reaction was terminated by adding ammonium chloride (1.97 g), an aqueous 20 wt % hydrogen chloride (3.18 g), and water (120 g). After phase separation of the reaction mixture and removal of the aqueous layer thus obtained, the organic layer containing (5Z)-5-hexadecen-1-ynyltrimethylsilane was washed with an aqueous 2 wt % ammonia (120 g). Next, the organic layer containing (5Z)-5-hexadecen-1-ynyltrimethylsilane obtained above, an aqueous 25 wt % sodium hydroxide solution (38.4 g), and methanol (200 g) were added to another reactor and stirred at from 50 to 55° C. for 12 hours. After phase separation of the reaction mixture and removal of the aqueous layer thus obtained, the organic layer was concentrated in a reduced pressure and the residue was subjected to distillation in a reduced pressure to obtain (5Z)-5-hexadecen-1-yne (4-4) (14.3 g, 0.0647 mol) in a yield of 80.8%.

(5Z)-5-Hexadecen-1-yne (4-4)

[Nuclear magnetic resonance spectrum] $^1$H-NMR (500 MHz, CDCl$_3$): δ 0.88 (3H, t, J=6.9 Hz), 1.26-1.36 (16H, m), 1.95 (1H, t, J=2.7 Hz), 2.04 (2H, td, J=6.9, 6.9 Hz), 2.20-2.24 (2H, m), 2.25-2.30 (2H, m), 5.37-5.49 (2H, m); $^{13}$C-NMR (75.6 MHz, CDCl$_3$): 14.10, 18.83, 22.68, 26.36, 27.30, 29.29, 29.34, 29.54, 29.63 (2C), 29.67, 31.90, 68.24, 84.21, 127.32, 131.67

[Mass spectrum] EI-Mass spectrum (70 eV): m/z 220 (M+), 135, 121, 107, 93, 79, 67, 55, 41, 29

[Infrared absorption spectrum] (NaCl): vmax 3313, 3009, 2955, 2924, 2854, 2121, 1466, 1378, 1246, 721, 631

Example 4

<Preparation of (5Z)-8-[(tetrahydro-2H-pyran-2-yl)oxy]-5-octen-1-yne (4-5)>

Magnesium (2.45 g, 0.101 gram atoms) and tetrahydrofuran (9.51 g) were added to a reactor and stirred at from 60 to 65° C. for 30 minutes. Then, (3Z)-1-chloro-6-[(tetrahydro-2H-pyran-2-yl)oxy]-3-hexene (1-5: $X^1$=Cl) (21.0 g, 0.0960 mol) was added dropwise at from 60 to 70° C. and the reaction mixture was stirred at from 70 to 75° C. for 6 hours to form (3Z)-6-[(tetrahydro-2H-pyran-2-yl)oxy]-3-hexenylmagnesium chloride. Next, dilithium tetrachlorocuprate (0.24 g, 0.0011 mol), (2-bromoethynyl)trimethylsilane (14.2 g, 0.0800 mol), and tetrahydrofuran (7.93 g) were added to another reactor, followed by stirring at from 5 to 10° C. for 10 minutes. Then, the aforesaid solution of the (3Z)-6-[(tetrahydro-2H-pyran-2-yl)oxy]-3-hexenylmagnesium chloride in tetrahydrofuran was added dropwise at from 30 to 35° C. After completion of the dropwise addition, the reaction mixture was stirred at from 30 to 35° C. for one hour and the reaction was then terminated by adding ammonium chloride (1.97 g), an aqueous 20 wt % hydrogen chloride (3.18 g), and water (120 g). After phase separation of the reaction mixture and removal of the aqueous layer thus obtained, the organic layer containing (5Z)-8-[(tetrahydro-2H-pyran-2-yl)oxy]-5-octen-1-ynyltrimethylsilane was washed with an aqueous 2 wt % ammonia (120 g). Next, the organic layer containing the (5Z)-8-[(tetrahydro-2H-pyran-2-yl)oxy]-5-octen-1-ynyltrimethylsilane obtained above, an aqueous 25 wt % sodium hydroxide solution (38.4 g), and methanol (80.0 g) were added to another reactor and stirred at from 53 to 58° C. for one hour. After phase separation of the reaction mixture and removal of the aqueous layer thus obtained, the organic layer was concentrated in a reduced pressure and the residue was subjected to distillation in a reduced pressure to obtain (5Z)-8-[(tetrahydro-2H-2-yl)oxy]-5-octen-1-yne (4-5) (12.2 g, 0.0588 mol) in a yield of 73.5%.

(5Z)-8-[(Tetrahydro-2H-pyran-2-yl)oxy]-5-octen-1-yne (4-5)

[Nuclear magnetic resonance spectrum] $^1$H-NMR (500 MHz, CDCl$_3$): δ 1.47-1.59 (4H, m), 1.66-1.72 (1H, m), 1.77-1.84 (1H, m), 1.94 (1H, t, J=2.7 Hz), 2.20-2.24 (2H, m), 2.26-2.32 (2H, m), 2.33-2.37 (2H, m), 3.37-3.42 (1H, m), 3.46-3.50 (1H, m), 3.70-3.75 (1H, m), 3.81-3.87 (1H, m), 4.58 (1H, dd, J=4.2, 2.7 Hz), 5.46-5.54 (2H, m); $^{13}$C-NMR (75.6 MHz, CDCl$_3$): 18.68, 19.51, 25.41, 26.38, 27.96, 30.63, 62.22, 66.86, 68.34, 84.01, 98.68, 127.35, 129.41

[Mass spectrum] EI-Mass spectrum (70 eV): m/z 208 (M+), 169, 115, 101, 85, 67, 55, 41, 29

[Infrared absorption spectrum] (NaCl): vmax 3298, 3012, 2942, 2869, 2118, 1454, 1441, 1385, 1352, 1323, 1201, 1137, 1121, 1077, 1033, 985, 906, 870, 814, 634

Example 5

<Preparation of (6Z)-1,1-diethoxy-6-nonen-2-yne (7a: two $R^6$s being $C_2H_5$)>

A solution (106 g, 0.274 mol) of methylmagnesium chloride (2.58 mmol/g) in tetrahydrofuran was added to a reactor and heated at from 40 to 45° C. for 10 minutes. Then, (5Z)-5-octen-1-yne (4-1) (19.7 g, 0.183 mol) was added dropwise at from 45 to 50° C. After completion of the dropwise addition, the reaction mixture was stirred at from 60 to 65° C. for 6 hours to form (5Z)-5-octen-1-ynylmagnesium chloride. Then, toluene (30.4 g) and ethyl orthoformate (40.6 g, 0.274 mol) were added to the reactor and stirred at from 90 to 95° C. for 5 hours. After cooling to a temperature of from 3 to 8° C., acetic acid (18.3 g) and water (119 g) were added to the reaction mixture. After phase separation of the reaction mixture and removal of the aqueous layer thus obtained, the organic layer was washed with an aqueous 8 wt % sodium hydroxide solution (29.8 g). The organic layer was concentrated in a reduced pressure and the residue was subjected to distillation in a reduced pressure to obtain (6Z)-1,1-diethoxy-6-nonen-2-yne (7a: two $R^6$s being $C_2H_5$) (23.6 g, 0.112 mol) in a yield of 61.5%.

(6Z)-1,1-Diethoxy-6-nonen-2-yne (7a: two $R^6$s being $C_2H_5$)

[Nuclear magnetic resonance spectrum] $^1$H-NMR (500 MHz, CDCl$_3$): δ 0.94 (3H, t, J=7.7 Hz), 1.21 (6H, t, J=7.3 Hz), 2.00-2.06 (2H, m), 2.25-2.26 (4H, m), 3.54 (1H, q, J=7.3 Hz), 3.56 (1H, q, J=7.3 HZ) 3.71 (1H, q, J=7.3 Hz), 3.73 (1H, q, J=7.3 Hz), 5.23 (1H, s), 5.36-5.31 (1H, m), 5.42 (1H, dt, J=10.7, 7.3 Hz); $^{13}$C-NMR (75.6 MHz, CDCl$_3$): 14.21, 15.03 (2C), 19.03, 20.51, 26.10, 60.52 (2C), 75.79, 85.92, 91.39, 126.82, 133.12

[Mass spectrum] EI-Mass spectral (70 eV): m/z 210 (M+), 181, 165, 136, 121, 107, 95, 81, 67, 55, 41, 29

[Infrared absorption spectrum] (NaCl): vmax 3008, 2975, 2932, 2884, 2242, 1444, 1391, 1329, 1150, 1082, 1054, 1007, 914, 719

Example 6

<Preparation of (2Z,6Z)-1,1-diethoxy-2,6-nonadiene (8: two $R^6$ being $C_2H_5$)>

(6Z)-1,1-diethoxy-6-nonen-2-yne (7a: two $R^6$s being $C_2H_5$) (23.3 g, 0.111 mol), a P-2Ni catalyst (3.74 g, 0.00197 mol as a nickel compound), and ethanol (71.0 g) were added to a reactor and heated to a temperature of from 45 to 50° C. Then, hydrogen was added and allowed to react for 3 hours.

After confirmation of the completion of the reaction, the reaction mixture was cooled to 30° C. and filtered to remove the P-2Ni catalyst.

Then, water (12.8 g) was added to the reaction mixture to wash it. The reaction mixture was phase-separated and the aqueous layer thus obtained was removed. The organic layer was concentrated in a reduced pressure to obtain (2Z,6Z)-1,1-diethoxy-2,6-nonadiene (8: two $R^6$ being $C_2H_5$) (19.9 g, 0.0935 mol) in a crude yield of 84.4%.

(2Z,6Z)-1,1-Diethoxy-2,6-nonadiene (8: two $R^6$s being $C_2H_5$)

[Nuclear magnetic resonance spectrum] $^1$H-NMR (500 MHz, CDCl$_3$): δ 0.94 (3H, t, J=7.7 Hz), 1.20 (6H, t, J=7.3 Hz), 2.00-2.06 (2H, m), 2.09-2.13 (2H, m), 2.16-2.21 (2H, m), 3.49 (1H, q, J=7.3 Hz), 3.51 (1H, q, J=7.3 Hz), 3.62 (1H, q, J=7.13 Hz), 3.64 (1H, q, J=7.3 Hz), 5.19 (1H, dd, J=6.9, 1.2 Hz), 5.28-5.34 (1H, m), 5.36-5.41 (1H, m), 5.48 (1H, ddt, J=11.1, 6.9, 1.2 Hz), 5.62 (1H, dtd, 11.1, 7.3, 1.2 Hz); $^{13}$C-NMR (75.6 MHz, CDCl$_3$): 14.24, 15.26 (2C), 20.50, 26.87, 28.10, 60.46 (2C), 97.65, 127.63, 127.90, 132.36, 134.02

[Mass spectrum] EI-Mass spectrum (70 eV): m/z, 212(M+), 183, 167, 155, 137, 121, 98, 85, 69, 57, 41, 29

[Infrared absorption spectrum] (NaCl): νmax 3007, 2974, 2932, 2876, 1658, 1456, 1389, 1317, 1122, 1054, 998, 890, 842, 723

Example 7

<Preparation of (2E,6Z)-2,6-nonadienal (9)>

(2Z,6Z)-1,1-diethoxy-2,6-nonadiene (8: two $R^6$s being $C_2H_5$) (8.20 g, 0.0386 mol) and water (2.82 g) were added to a reactor and stirred at from 3 to 8° C. for 10 minutes. Then, an aqueous 20 wt % hydrogen chloride (3.99 g) was added dropwise at from 3 to 8° C., followed by stirring at from 20 to 25° C. for 2 hours. Subsequently, it was confirmed using a pH test strip that the aqueous layer had a pH of less than 1. Then, hexane (3.28 g) was added and the resulting reaction mixture was phase-separated. After removal of the aqueous layer, the organic layer was washed with salt (0.08 g) and water (3.19 g). The organic layer was concentrated in a reduced pressure and the residue was purified by silica gel column chromatography (n-hexane/ethyl acetate=20/1→14/1) to obtain (2E,6Z)-2,6-nonadienal (9) (4.98 g, 0.0360 mol) in a yield of 93.2%.

(2E,6Z)-2,6-Nonadienal (9)

[Nuclear magnetic resonance spectrum] $^1$H-NMR (500 MHz, CDCl$_3$): δ 0.94 (3H, t, J=7.7 Hz), 2.02 (2H, dt, J=7.7, 7.3 Hz), 2.24 (2H, td, J=7.3, 7.3 Hz), 2.38 (2H, tdd, J=7.3, 7.3, 1.5 Hz), 5.26-5.31 (1H, m), 5.40-5.45 (1H, m), 6.11 (1H, ddt, J=15.7, 8.0, 1.5 Hz), 6.82 (1H, dt, J=15.7, 6.9 Hz), 9.48 (1H, d, J=8.0 Hz); $^{13}$C-NMR (75.6 MHz, CDCl$_3$): 14.12, 20.50, 25.35, 32.66, 126.66, 133.14, 133.23, 158.01, 193.95

[Mass spectrum] EI-Mass spectrum (70 eV): m/z 138 (M+), 123, 109, 95, 81, 67, 53, 41, 27

[Infrared absorption spectrum] (NaCl): νmax 3008, 2964, 2934, 2874, 2735, 1694, 1638, 1456, 1303, 1175, 1133, 1105, 973, 719, 565

Example 8

<Preparation of (2E)-cis-6,7-epoxy-2-nonenal (10)>

(2E,6Z)-2,6-nonadienal (9) (4.73 g, 0.0342 mol) and dichloromethane (226 g) were added to a reactor and stirred at from −5 to 0° C., for 10 minutes. Then, meta-chloroperbenzoic acid (7.08 g, 0.0411 mol) was added and the resulting mixture was stirred at from −5 to 0° C. for 4 hours. Then, the reaction was terminated by adding sodium thiosulfate (3.25 g) and an aqueous 4 wt % sodium hydroxide solution (35.0 g) to the reaction mixture. The reaction mixture was phase-separated and then, the aqueous layer thus obtained was removed. The organic layer was washed with saturated saline (80 ml), followed by phase-separation and removal of the aqueous layer again. The organic layer was concentrated in a reduced pressure and the residue was purified by silica gel column chromatography (n-hexane/ethyl acetate=9/1→3/1) to obtain (2E)-cis-6,7-epoxy-2-nonenal (10) (4.49 g, 0.0291 mol) in a yield of 85.0%.

(2E)-cis-6,7-Epoxy-2-nonenal (10)

[Nuclear magnetic resonance spectrum] $^1$H-NMR (500 MHz CDCl$_3$): δ 1.01 (3H, t, J=7.7 Hz), 1.43-1.59 (2H, m), 1.61-1.68 (1H, m), 1.73-1.80 (1H, m), 2.44-2.57 (2H, m), 2.88 (1H, td, J=6.5, 4.2 Hz), 2.92 (1H, td, J=7.3, 4.2 Hz), 6.13 (1H, ddt, J=15.7, 7.7, 1.5 Hz), 6.87 (1H, dt, J=15.7, 6.9 Hz), 9.49 (1H, d, J=7.7 Hz); $^{13}$C-NMR (75.6 MHz, CDCl$_3$): 10.47, 21.02, 26.15, 29.80, 56.17, 58.26, 133.27, 156.85, 193.72

[Mass spectrum] EI-Mass spectrum (70 eV): m/z 154 (M+), 136, 125, 112, 97, 85, 67, 55, 41, 29

[Infrared absorption spectrum] (NaCl): νmax 2972, 2937, 2878, 2818, 2737, 1691, 1638, 1458, 1391, 1308, 1273, 1130, 1095, 1016, 976, 905, 816

The invention claimed is:

1. A process for preparing a 5-alken-1-yne compound of the following formula (4):

$$Y-Z-CR^1=CR^2-(CH_2)_2-C\equiv CH \quad (4)$$

in which Y in formula (4) represents a hydrogen atom or a hydroxyl group, Z represents a divalent hydrocarbon group having from 1 to 15 carbon atoms, and $R^1$ and $R^2$ represent, each independently, a hydrogen atom or a monovalent hydrocarbon group having from 1 to 6 carbon atoms or bond together to form a divalent hydrocarbon group having from 1 to 6 carbon atoms, $R^1$-$R^2$, the process comprising at least steps of:
subjecting (i) an alkenylmagnesium halide compound prepared from a haloalkene compound of the following formula (1):

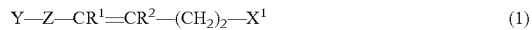
$$Y-Z-CR^1=CR^2-(CH_2)_2-X^1 \quad (1)$$

in which Y, Z, $R^1$ and $R^2$ are as defined above and $X^1$ represents a halogen atom, and (ii) an alkyne compound of the following formula (2):

$$X^2-C\equiv C-Si(R^3)(R^4)(R^5) \quad (2)$$

in which $X^2$ represents a halogen atom, $R^3$ represents a hydrogen atom or a monovalent hydrocarbon group having from 1 to 6 carbon atoms, and $R^4$ and $R^5$ represent, each independently, a monovalent hydrocarbon group having from 1 to 6 carbon atoms or bond together to represent a divalent hydrocarbon group having from 2 to 6 carbon atoms, $R^4$-$R^5$, to a coupling reaction to form a silane compound of the following formula (3):

$$Y-Z-CR^1=CR^2-(CH_2)_2-C\equiv C-Si(R^3)(R^4)(R^5) \quad (3)$$

in which Y, Z, $R^1$, $R^2$, $R^3$, $R^4$, and $R^5$ are as defined above; and
subjecting the silane compound (3) to a desilylation reaction to form the 5-alken-1-yne compound (4).

2. The process according to claim 1, wherein the haloalkene compound (1) is a (3Z)-1-halo-3-hexene compound of the following formula (1-1), Y in formula (1) represents a hydrogen atom, Z represents an ethylene group, and $R^1$ and $R^2$ each represent a hydrogen atom:

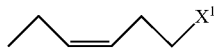 (1-1)

in which $X^1$ represents a halogen atom;
the silane compound (3) is a silane compound of the following formula (3-1):

 (3-1)

in which $R^3$, $R^4$, and $R^5$ are as defined above; and
the 5-alken-1-yne compound (4) is (5Z)-5-octen-1-yne of the following formula (4-1):

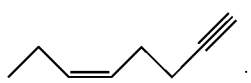 (4-1)

3. A process for preparing a (6Z)-1,1-dialkoxy-6-nonen-2-yne compound of the following formula (7a):

 (7a)

in which $R^6$ may be the same or different at each occurrence and represents a monovalent hydrocarbon group having from 1 to 6 carbon atoms,
the process comprising at least steps of:
each of the steps of the process according to claim 2 for preparing (5Z)-5-octen-1-yne of the following formula (4-1):

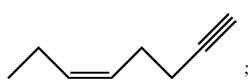 (4-1)

preparing, from the (5Z)-5-octen-1-yne (4-1) thus obtained, an acetylide compound of the following formula (5):

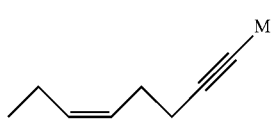 (5)

in which M represents Li, Na, K, or $MgX^3$, and $X^3$ represents a halogen atom; and
subjecting the acetylide compound (5) and an orthoformic acid ester compound of the following formula (6):

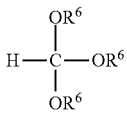 (6)

in which $R^6$ may be the same or different at each occurrence and represents a monovalent hydrocarbon group having from 1 to 6 carbon atoms, to a nucleophilic substitution reaction to form the (6Z)-1,1-dialkoxy-6-nonen-2-yne compound (7a).

4. A process for preparing a process for preparing (2E, 6Z)-2,6-nonadienal of the following formula (9):

 (9)

the process comprising at least steps of:
each of the steps of the process according to claim 3 for preparing (6Z)-1,1-dialkoxy-6-nonen-2-yne compound (7a);
subjecting the (6Z)-1,1-dialkoxy-6-nonen-2-yne compound (7a) thus obtained to a reduction reaction to form a (6Z)-1,1-dialkoxy-2,6-nonadiene compound of the following formula (8):

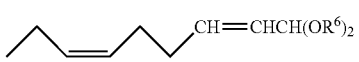 (8)

in which $R^6$ may be the same or different at each occurrence and represents a monovalent hydrocarbon group having from 1 to 6 carbon atoms; and
hydrolyzing the (6Z)-1,1-dialkoxy-2,6-nonadiene compound (8) to form (2E,6Z)-2,6-nonadienal (9).

5. A process for preparing (2E)-cis-6,7-epoxy-2-nonenal of the following formula (10):

 (10)

the process comprising at least steps of:
each of the steps of the process according to claim 4 for preparing (2E,6Z)-2,6-nonadienal (9); and
epoxidizing the (2E,6Z)-2,6-nonadienal (9) thus obtained to form (2E)-cis-6,7-epoxy-2-nonenal (10).

* * * * *

UNITED STATES PATENT AND TRADEMARK OFFICE
CERTIFICATE OF CORRECTION

PATENT NO. : 10,781,146 B2
APPLICATION NO. : 16/533254
DATED : September 22, 2020
INVENTOR(S) : Watanabe et al.

It is certified that error appears in the above-identified patent and that said Letters Patent is hereby corrected as shown below:

In the Specification

Column 10, Line 27, middle of Formula 4-2:
Please correct "$CH_3–CH_2–CH=CH–(CH_2)_2–C\equiv C–(R^3)(R^4)(R^5)$"
To read -- $CH_3–CH_2–CH=CH–(CH_2)_2–C\equiv C–Si(R^3)(R^4)(R^5)$ --

Column 14, Lines 25-29:

Please correct " 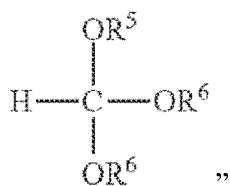 "

To read -- 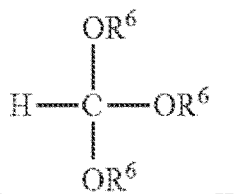 --

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*